United States Patent [19]

Martin et al.

[11] Patent Number: 5,460,978
[45] Date of Patent: Oct. 24, 1995

[54] PROTEIN ACTIVE IN HUMORAL HYPERCALCEMIA OF MALIGNANCY-PTHRP

[75] Inventors: Thomas J. Martin, Kew; Jane M. Moseley, North Balwyn; Bruce E. Kemp, Kew; Richard E. H. Wettenhall, Camberwell, all of Australia

[73] Assignee: The University of Melbourne, Parkville, Australia

[21] Appl. No.: 715,280

[22] Filed: Jun. 14, 1991

Related U.S. Application Data

[62] Division of Ser. No. 199,235, May 9, 1988, Pat. No. 5,116,952 which is a stage of PCT/AU87/00165, Jun. 4, 1987.

[30] Foreign Application Priority Data

Jul. 18, 1986 [AU] Australia .............................. PH7027/86
Feb. 13, 1987 [AU] Australia .............................. PI0349/87

[51] Int. Cl.⁶ ................................................. G01N 33/53
[52] U.S. Cl. .................................................. 436/518; 435/7.1
[58] Field of Search ..................................... 436/518; 435/7.1

[56] References Cited

U.S. PATENT DOCUMENTS

| | | | |
|---|---|---|---|
| 3,886,132 | 5/1975 | Brewer et al. | 530/324 |
| 4,086,196 | 4/1978 | Tregear | 330/334 |
| 4,105,602 | 8/1978 | Colescott et al. | 524/577 |
| 4,391,904 | 7/1983 | Litman et al. | 435/7.91 |
| 4,409,141 | 10/1983 | Noda et al. | 530/324 |
| 5,116,952 | 5/1992 | Martin et al. | 530/399 |

OTHER PUBLICATIONS

M. Ellison et al, Immunoreactive Calcitonin Production by Human Lung Carcinoma Cells in Culture. Br. J. Cancer 32, 373–379, 1975.
N. H. Hunt et al, Calcitonin–responsive Adenylate Cyclase in a Calcitonin–producing Human Cancer Cell Line. Br. J. Cancer (1977) 35, 777–782, 1977.
T. J. Martin et al, Hormone Receptors and Cyclic Nucleotide Metabolism in Cancer Cells. Clinical Endocrinology 5, Suppl., 373s–386s, 1976.
D. M. Findlay et al, Properties of a Calcitonin Receptor and Adenylate Cyclase in BEN Cells, A Human Cancer Cell Line. Cancer Research 40, 1311–1317, 1980.
V. P. Michelangeli et al, Mechanisms of Calcitonin Induction of Prolonged Activation of Adenylate Cyclase in Human Can. Cells. Journ. of Cyclic Nucleotide & Protein Phosphorylation Res.9:129–142 1983.
J. M. Moseley et al, Photoaffinity Labeling of the Calcitonin Receptor. Pharmac. Ther. vol. 34, pp. 51–58, 1987.
J. D. Zajac et al, Biosynthesis of Calcitonin by Human Lung Cancer Cells. Endocrinology 116:749–755, 1985.
D. M. Findlay et al, Protein Kinase–C–Induced Down–Regulation of Calcitonin Receptors and Calcitonin14 Activated Adenylate Cyclase in T47D and BEN Cells. Endocrinology 125:2656–2662, 1989.
D. T. Brown et al, Monoclonal Antibodies Against Two Human Lung Carcinoma Cell Lines. Br. J. Cancer 46:794–800, 1982.
L. Pizurki et al, Factor Derived fr. Human Lung Carcinoma Assoc. w/Hypercalcemia Mimics the Effects of Parathyroid Hormone on Phosphate Transp. in Cult. Renal Epith. Jour. of Bone & Min. Res. 3, 1988.
S. Murray et al, The Coregulation of Secretion and Cytoplasmic Ribonucleic Acid of Chromagranin–A Calcitonin by Phorbol Ester in Cells that Produce both Substances. Endocrinology 122:495–502, 1988.

(List continued on next page.)

*Primary Examiner*—Keith C. Furman
*Attorney, Agent, or Firm*—Sughrue, Mion, Zinn, Macpeak & Seas

[57] ABSTRACT

Substantially pure parathyroid hormone related protein (PTHrP) active in humoral hypercalcemia of malignancy and sub-units and fragments thereof. Antibody reagents capable of binding to epitopes of PTHrP. Methods and kits for the detection of PTHrP.

6 Claims, 8 Drawing Sheets

OTHER PUBLICATIONS

L. J. Deftos et al, The Parathyroid Hormone–Related Protein Associated with Malignancy is Secreted by Neuroendocrine Tumors. Molecular Endocrinology Endocrinology 3:503–508, 1989.

M. Mangin et al, Identification of an Up–Stream Promoter of the Human Parathyroid Hormone–Related Peptide Gene. Molecular Endocrinology 4:851–858, 1990.

Stewart, F. et al, *Proc. Natl. Acad. Sci. USA,* vol. 80, pp. 1454–1458 (1983).

Rodan, S. et al, *J. Clin. Invest.,* vol. 72, pp. 1511–1515 (1983).

Strewler, G. et al, *J. Clin. Invest.,* vol. 71, pp. 769–774 (1983).

Merendino, J. et al, *Science,* vol. 231, pp. 388–390 (1986).

Rosol, T. et al, *Laboratory Investigation,* vol. 54, No. 6, pp. 679–687 (1986).

MAJOR 7 : ATSEVTPNGKPQ(P)(R) (SEE 38-51)
MINOR 7 : YLPQER (SEE 54-59)
     12 : AVS
     14 : YLTQEINKVE T/F Y K (SEE 68-80)

PROTEIN ACTIVE IN HUMORAL HYPERCALCEMIA OF MALIGNANCY-PTHRP

This is a divisional of application No. 07/199,235, filed May 9, 1988, now Pat. No. 5,116,952 which is the stage of PCT/AU87/00165, Jun. 4, 1987.

The present invention relates to proteins active in humoral hypercalcemia of malignancy hereinafter referred to as PTHrP (parathyroid hormone related hormone), ACSF (adenylate cyclase stimulating factor), or BRF (bone releasing factor).

The invention further relates to peptide fragments of ACSF and to the purification and partial sequence determination of PTHrP. The invention also relates to antibodies directed against PTHrP or fragments thereof and kits containing said antibodies useful in the identification of PTHrP. [NOTE: Literature references cited herein are given in full at the end of the specification.]

Humoral hypercalcemia of malignancy (HHM) is a very common complication of certain cancers, especially squamous cell carcinoma of the lung, in which it contributes substantially to morbidity and mortality (1,2). Cancer-derived humoral factors can elevate blood calcium levels by promoting bone resorption and restricting calcium excretion by the kidney (1–3). Although it was thought for many years that "ectopic" production of parathyroid hormone (PTH) by these cancers was the cause of the HHM syndrome (4,5), it has become apparent that factors other than PTH are responsible (1–3,6–8), including transforming growth factors (TGF's), which are potent promoters of bone resorption (2,3,9–11). There is also evidence for the production by certain cancers of some factor immunologically distinct from PTH, but which resembles PTH in stimulating adenylate cyclase activity in PTH target cells (kidney and bone), by acting either directly on the PTH receptor or on a closely related membrane component. Such a possibility was suspected on the basis of clinical evidence (7), and the activity has been noted in extracts of tumors from patients with HHM (12,13), in conditioned medium from a renal cortical carcinoma cell (14), in tumour extracts and culture conditioned media from animal models of HHM (15,16).

We have found that the BEN cell line, originally established from a hypercalcemic patient with a squamous cell carcinoma of the bronchus (17), produces appreciable amounts of this PTH-like activity, hereinbefore described as PTHrP, that stimulates adenylate cyclase in osteoblast-like cells.

We have now succeeded in purifying and characterizing PTHrP.

According to one aspect of the present invention, there is provided substantially pure PTHrP as hereinafter defined.

According to a further aspect of the present invention, there is provided fragments or sub-units of PTHrP, having PTHrP activity.

The isolation and purification of PTHrP will enable investigations to be carried out to characterize its role in the humoral hypercalcemia of malignancy.

PTHrP or peptide fragments thereof may be used to produce both monoclonal and polyclonal antibody reagents, by methods known per se in the art. For example, antibody reagents may be prepared by immunizing appropriate host animals with PTBrP or peptide fragments thereof either alone or in the presence of adjuvants and/or carrier proteins. Examples of appropriate hosts include mice, rats, rabbits, sheep, horses, goats and cows. Where monoclonal antibody reagents are produced, the techniques generally employed are according to the procedure set out by Kohler et al. (18) and Kennet et al (19).

Antibody reagents directed against PTMrP can be utilized in assays to detect PTHrP activity, for example in whole blood, blood plasma, or other biological fluids. Particularly, such reagents will be of considerable utility in the investigation of, and as an aid to diagnosis in, patients with cancer, chronic renal failure, and other bone diseases in which PTH itself is thought to play a role.

Antibodies prepared against PTHrP and peptide fragments thereof, are also useful as immunohistochemical diagnostic reagents, for the immunolocalization of cells capable of producing PTHrP in various tissues.

For diagnostic purposes, antibody reagents may comprise antibodies directed against PTHrP which have been suitably labelled, with a detectable marker, for example; rhodamine, fluorescein, colloidal gold, horseradish peroxidase, $\beta$-galactosidase, urease, alkaline phosphatase, phycobiliproteins, luciferase, ferritin, $^{125}I$, $^{32}P$, $^{3}H$ or $^{14}C$.

We have raised antibodies against synthetic peptides of PTHrP. These antibodies may be used to detect PTHrP or fragments thereof by, for example, radioimmunoassay (50) or by western blotting techniques (51). PTHrP produced by cultured tumour cells in vitro or by tumours in vivo may be detected using these antibodies or other antibody reagents directed against PTHrP.

According to a further aspect of the present invention, there is provided antibody reagents directed against PTHrP and fragments thereof.

According to a still further aspect of the present invention, there is provided a kit for the detection of PTHrP or fragments thereof comprising one or more antibody reagents capable of binding to epitopes of PTHrP.

The kits provided by the present invention may contain antibodies directed against PTHrP which have been labelled, for example with fluorescent, radioactive or proteinaceous labels as mentioned above. Kits may also contain one or more labelled secondary or tertiary antibodies. Additionally, kits may contain buffers for the dilution of reagents, and various supports such as dishes or trays for the carrying out of assays. Antibodies directed against PTHrP or fragments thereof may be freeze dried, and thus in a powdered form suitable for suspension in an appropriate aqueous solution. Alternatively, the antibodies may be present in an aqueous solution suitable for storage.

According to a further aspect of the present invention, there is provided a method for the detection of PTHrP or fragments thereof in a given protein containing sample comprising; contacting the sample, or support onto which protein in the sample is immobilized, with antibody reagents capable of binding to epitopes of PTHrP; and subsequently detecting the presence or absence of antibody binding.

According to another aspect of the present invention there is provided a method for the detection of PTHrP or fragments thereof in a given sample comprising; incubating the sample with a support onto which are bound antibodies capable of binding epitopes of PTHrP, for a time sufficient to allow antibody binding, and thereafter detecting the presence or absence of bound PTHrP with antibody reagents capable of binding epitopes of PTHrP.

The purification of PTHrP and determination of the N-terminal amino acid sequence thereof will enable synthetic oligonucleotides to be produced corresponding to the amino acid sequence of PTHrP. These oligonucleotides may then be used as hybridization probes, thus facilitating the isolation of the gone or genes encoding PTHrP. Such oligonucleotides may also be used as diagnostic reagents, and also to detect the expression of mRNA encoding PTHrP and in investigations of control of the expression of the gone or genes encoding PTHrP.

PTHrP produced by the human tumour line BEN exists in two forms, having identical biological activity, but distinguishable on the basis of immuno-crossreactivity, molecular weight and elution behaviour on HPLC. Both of these forms of PTHrP, are within the scope of the present invention.

According to a further aspect of the present invention PTHrP is obtained from medium in which BEN cells have been cultured. More specifically, one method for the purification of PTHrP comprises the following steps:

(a) culturing BEN cells in culture medium;

(b) applying the culture medium to a cation exchange resin;

(c) eluting fractions from the cation exchange resin;

(d) assaying the eluted fractions for PTHrP activity;

(e) performing reverse phase high performance liquid chromatography (HPLC) on those fractions possessing PTHrP activity and subsequently isolating substantially pure PTHrP.

BRIEF DESCRIPTION OF THE DRAWINGS

Various aspects of the present invention will now be described in more detail, by way of example only with reference to the accompanying drawings, in which.

A. 220 μg of pooled peak B material from VYDAC HPLC was applied to a $C_{18}$ BAKERBOND column (25×0.46 cm). Elution was carried out using a gradient of 0–60% acetonitrile/0.1% TFA at a rate of 0.66% per minute. Fractions were collected according to protein peaks observed at 215 run. Adenylate cyclase activity was assayed in 10 μl aliquots from each fraction and values adjusted for fraction volumes.

B. 6 μg of hPTH (1–34) equivalents pooled from run A (fractions 51–55) were reapplied to the column of run A above and eluted in a gradient of 0–68% acetonitrile/ 0.9% TFA at a rate of 0.33% per minute.

Figure 1A:
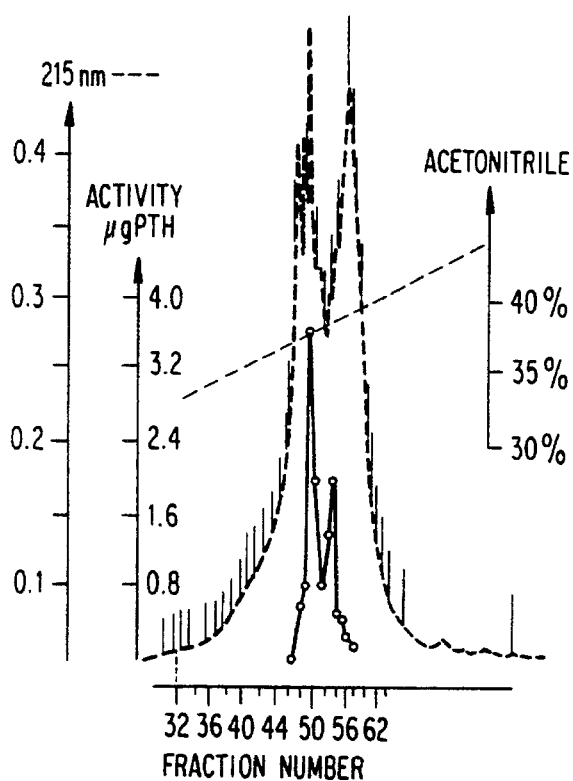
FIGS. 1A and 1B show an HPLC profiles of adsorbance at 215 nm and biological activity, at the final purification step of PTHrP.
Figure 1B:
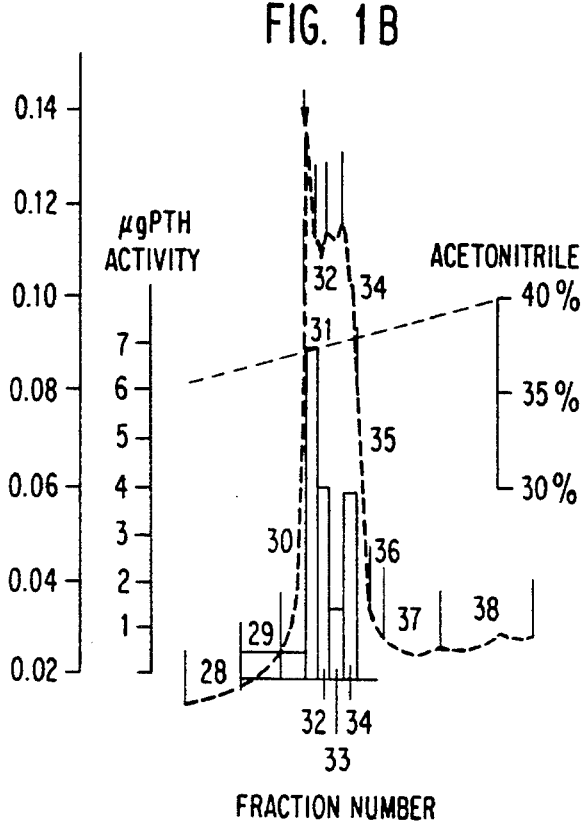
Figure 2:
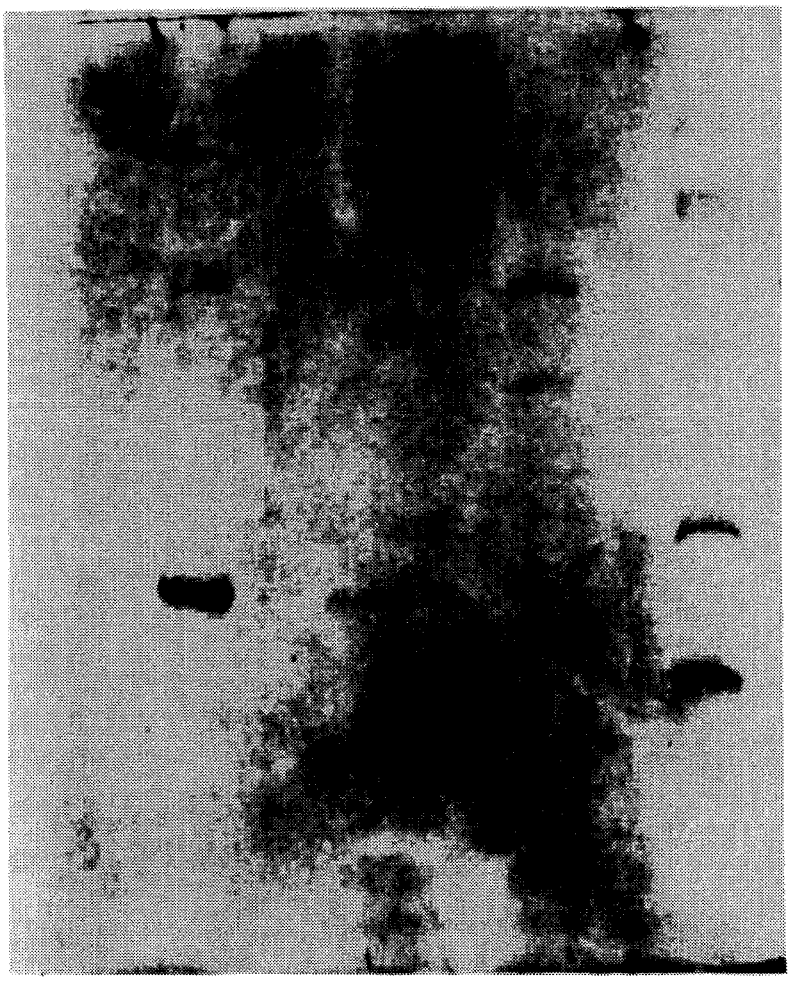
Figure 3:
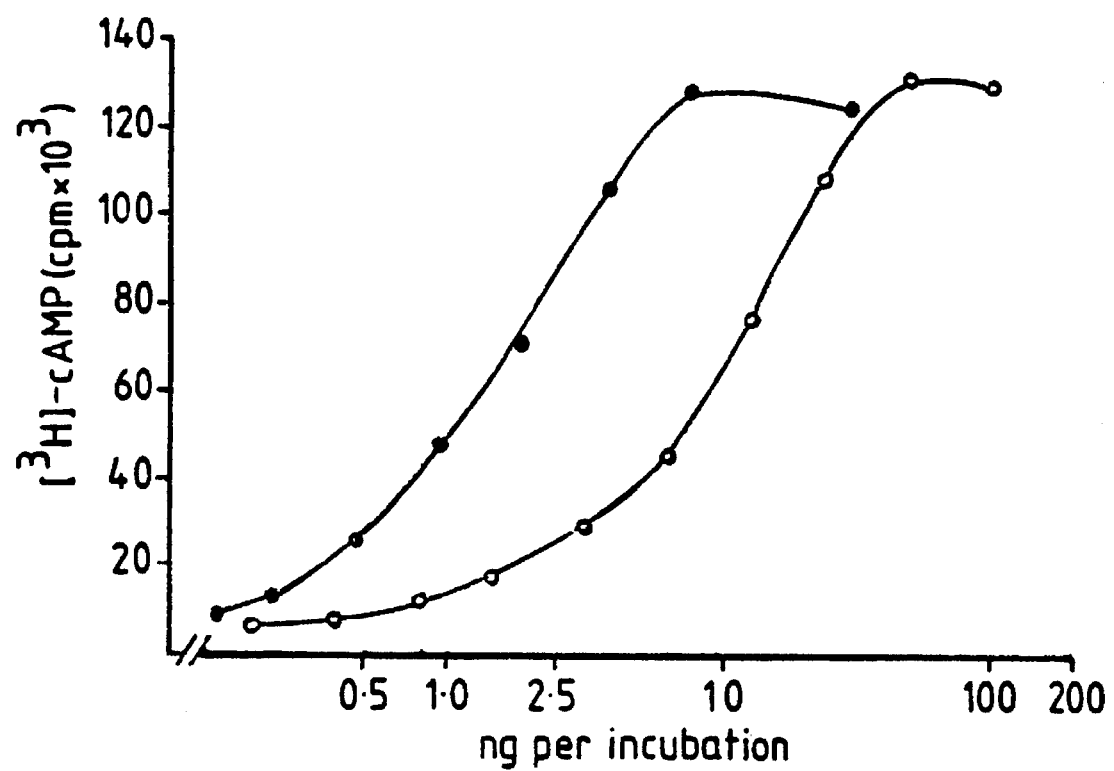
Figure 4:
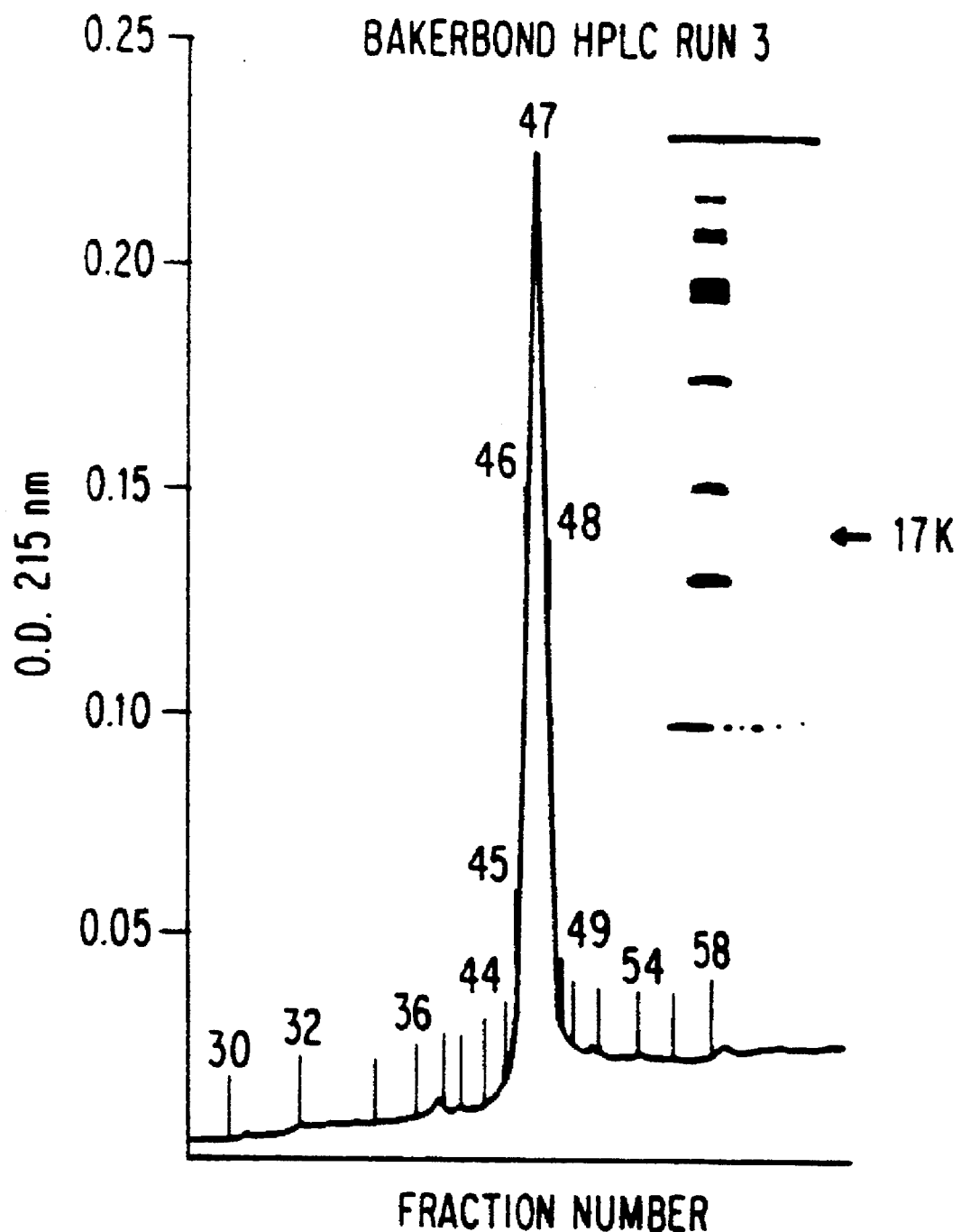

FIG. 2 shows an SDS polyacrylamide gel of fractions 31, 32 and 34 of FIG. 1;

FIG. 3 shows a plot of the biological activity of fraction 31 (●) of FIG. 1, assayed against bovine PTH(1–34) (o) in intact UMR 106 cells;

FIG. 4 shows an HPLC profile of purified PTHrP, obtained after SP SEPHADEX chromatography (SEPHADEX is a cross-linked exchange gel) and two BAKERBOND chromatographic steps, chromatographed on a reversed phase HPLC column (Bakerbond C18 widepore 25×0.46 cm). The inset shows SDS-PAGE silver-stained gel profiles of fraction 47 and molecular weight standards.

Figure 5:
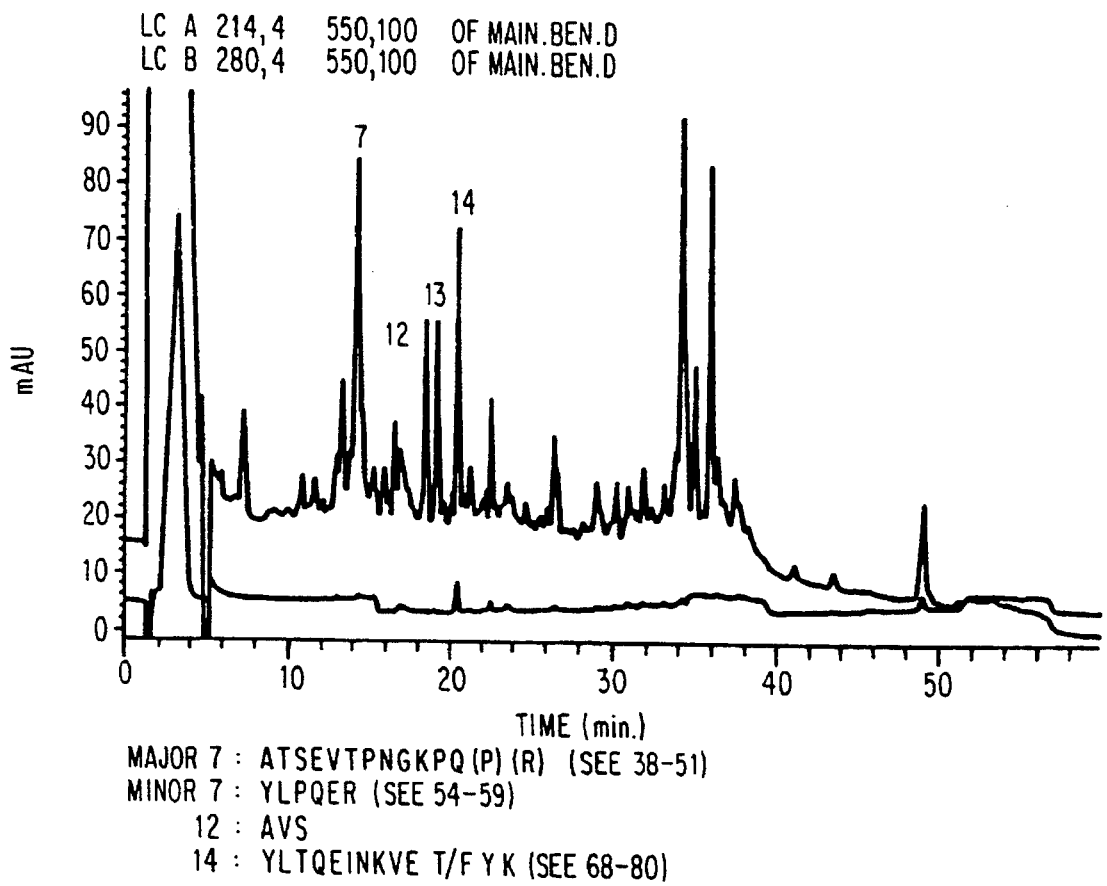

FIG. 5 shows an HPLC profile of PTHrP (100 pMoles) after digestion with trypsin. The tryptic digest was chromatographed on a C8 BROWNLEE cartridge, 10 cm×2.1 mm, at a flow rate of 250 μl/min. A 0–50% acetonitrile in 0.1% TFA gradient (1%/min) was employed.

Figure 6:
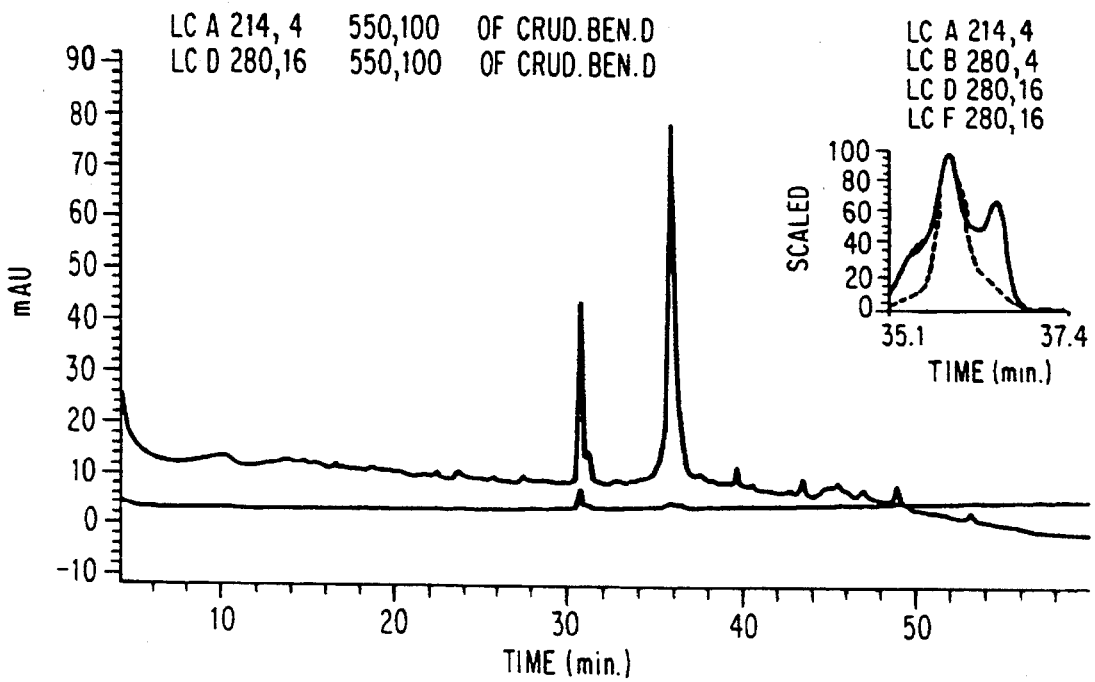

FIG. 6 shows the pooled material of fractions 46 and 48 of FIG. 4 chromatographed on a BROWNLEE C8 (2.1 mm) microbore column. The inset shows diode array detection of the major peak.

Figure 7A:
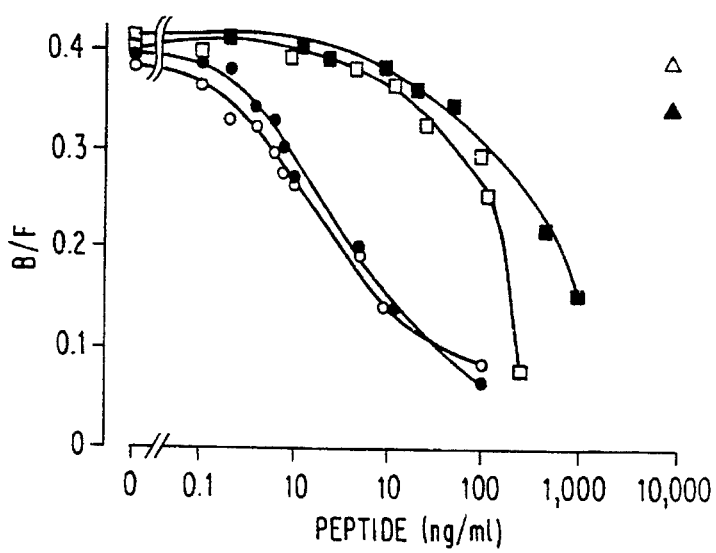
Figure 7B:
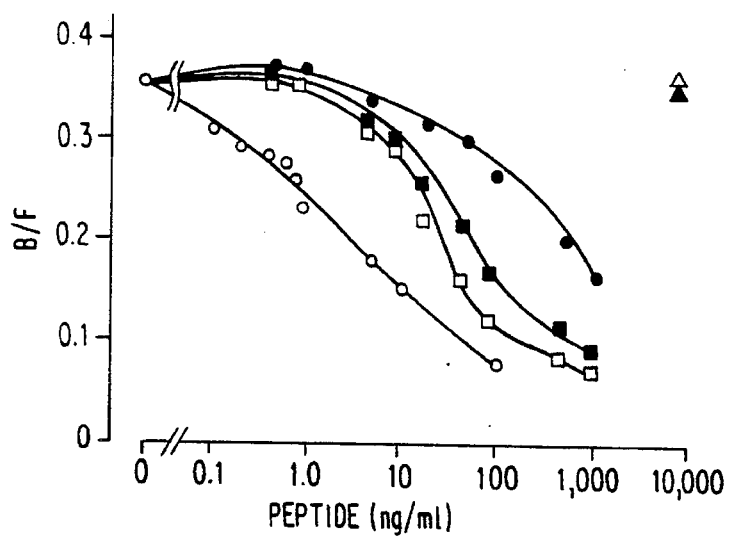

FIGS. 7A and 7B show a radio immunoassays using various unlabelled peptides, $I^{125}$ labelled [$Asn^{10}$, $Tyr^{17}$] PTHrP (1–17) as tracer and rabbit antiserum to the synthetic PTHrP (1–17) peptide. Bound peptide/free peptide is plotted against amount of peptide/ml.

FIG. 7A: Unlabelled peptides were: [$Glu^8$,$Asn^{10}$,$Cys^{11}$]PTHrP(1–11)(o), [$Asn^{10}$] PTHrP(1–16) (●), hPTH(1–10) (□), hPTH(1–34) (■), rat calcitonin gene-related peptide (CGRP), human adrenocorticotropin and bovine insulin (all at 10 μg/ml,△), salmon calcitonin (10 μg/ml,▲).

FIG. 7B: Unlabelled peptides were: [$Glu^8$,$Asn^{10}$, $Cys^{11}$] PTHrP(1–11)(O), rat PTH(1–34)(□), bovine PTH(1–34) (■), human PTH(1–34) (●), rat CGRP (10 μg/ml,△), salmon calcitonin (10 μg/ml,▲).

Figure 8:
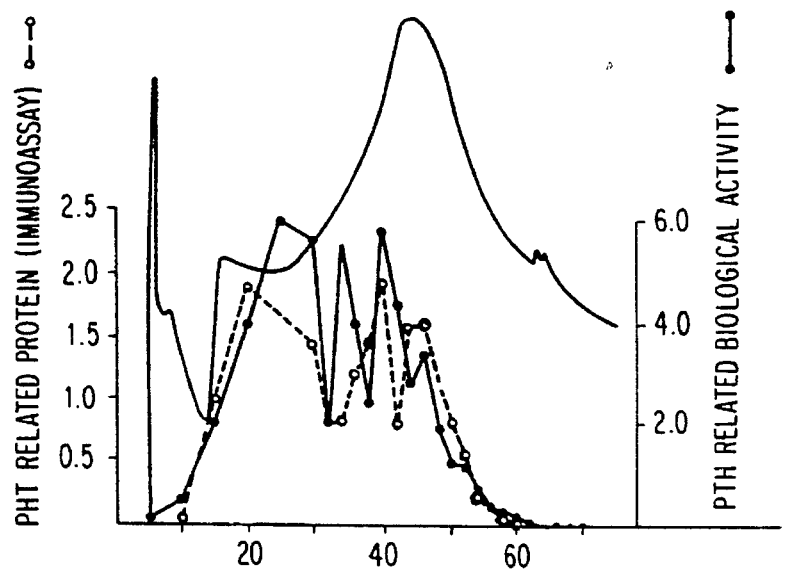

FIG. 8 shows a comparison of biological assay (o) and radioimmunoassay (●) of fractions from HPLC of SP-SEPHADEX partially purified PTHrP.

Figure 9A:
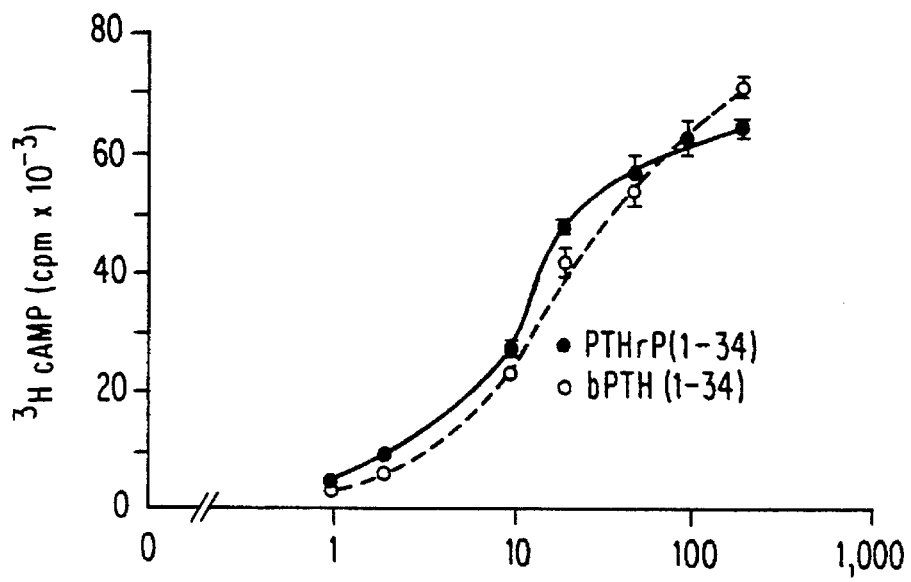
Figure 9B:
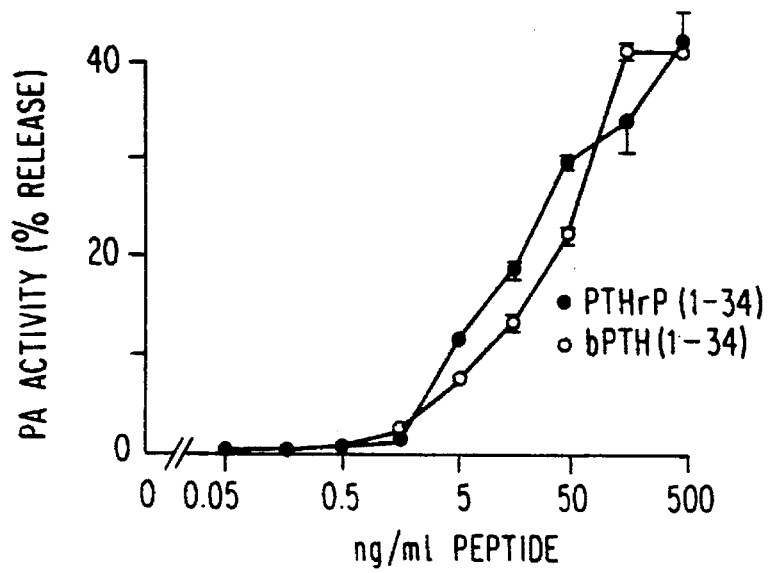

FIGS. 9A and 9B show:

FIG. 9A shows: Biological activity of synthetic PTHrP(1–34) (●) in increasing cyclic AMP production in UKR 106-01 cells compared with bovine PTH (1–34) (O) as standard; and FIG. 9B shows: Effect of synthetic PTHrP (1–34) (●) and bovine PTH (1–34) (O) on plasminogen activator activity in UMR 106-01 cells plated on $^{125}$I-fibrin. The assay was carried out according to the previously described method of Allan et al (52).

Figure 10:
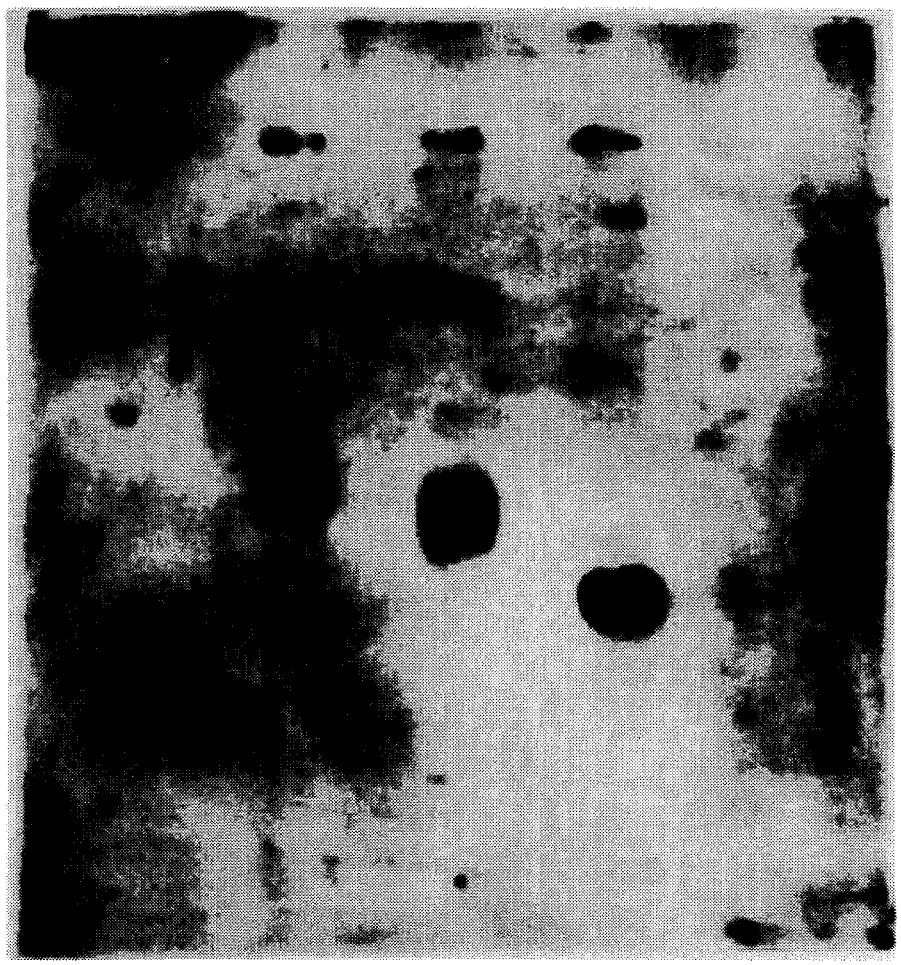

FIG. 10 shows a western blot analysis of PTHrP protein from two samples of peak A of Example 3 (A1 and A2, lanes 2 and 3), highly purified bovine parathyroid hormone (lane 1), and highly purified PTHrP derived from peak B of Example 3 (lane 4). Samples were separated on SDS-PAGE, transferred to nitrocellulose; probed with rabbit antiserum raised against PTHrP (1–16); washed and incubated with $^{125}$I-labelled Fab fragments of goat anti-rabbit $IgG_1$, and autoradiographed. Molecular weight standards are designated with horizontal arrows.

Definitions:

"PTHrP" refers to a protein active in humoral hypercalcemia of malignancy, having a molecular weight between 15,000 and 25,000 daltons, as determined by SDS polyacrylamide gel electrophoresis, and active in stimulating adenylate cyclase activity in appropriate target cells (such as UMR 106-01 cells), in a manner similar to parathyroid hormone.

As mentioned previously, PTMrP purified from BEN cells is polymorphic and exists in two discernable forms having substantially identical biological activity. One of these forms has a molecular weight between 15–18K as determined by SDS-PAGE, and an N-terminal sequence set forth in Table 1. The other form, has a molecular weight between 18K–25K. This second form cross-reacts with antisera prepared against the first-mentioned form of PTHrP. Both forms of PTHrP are within the scope of the present invention and are embraced by the term "PTHrP".

Further, allelic variants of PTHrP, which possess PTHrP activity, are within the scope of the present invention and are also embraced by the term "PTHrP". Such variants are represented by the deletion, substitution or addition of amino acid(s) to the sequence of PTHrP, which is represented (in part) in Table 1. Variants, where the naturally occuring amino acids as represented by Table 1 are deleted and/or substituted with other amino acids, or further amino acids are added to the natural sequence of PTHrP, may be produced by conventional protein synthesis techniques (41) or by recombinant DNA technology (53). Such variants, which possess PTHrP activity, are within the scope of the present invention and are also embraced by the term "PTHrP".

"Substantially pure" when used in relation to PTHrP refers to PTHrP when essentially free of protein or other contaminant material normally associated with PTHrP; generally giving rise to a single band on SDS-PAGE; and generally wherein from about 95% to 100%, ordinarily about 97%, by weight of the total protein is PTHrP. "PTHrP" according to the practice of this invention, is distinguishable from crude uncharacterized preparations of material having PTH-like activity as described in the prior art. The prior art preparations (54 and 55) consisted of a large number of proteins, with the active factor being present in very small amounts compared to the total amount of protein and other material. These preparations were unsuitable for protein sequence analysis or for the production of antibodies specific for PTHrP.

The terms "sub-unit" or "fragment" are used herein to refer to portions of the PTHrP protein, which are unique to PTHrP. As will be appreciated, this specifically excludes a single amino acid. Generally, peptides of less than 5 amino acids in length will not be unique.

"Epitope" refers to any antigenic portion of PTHrP or fragments or sub-units thereof capable of eliciting an immune response.

| Abbreviations: | |
| --- | --- |
| HPLC | High performance liquid chromatography |
| SDS-PAGE | Sodium dodecyl polyacrylamide gel electrophoresis |
| PTH | Parathyroid hormone |
| hPTH | Human parathyroid hormone |
| PTHrP(1–11) | A synthetic peptide of PTHrP corresponding to amino acids 1 to 11 of Table 1 |
| PTHrP(1–16) | A synthetic peptide of PTHrP corresponding to amino acids 1 to 16 of Table 1 |
| PTHrP(1–17) | A synthetic peptide of PTHrP corresponding to amino acids 1 to 17 of Table 1 |
| PTHrP(1–34) | A synthetic peptide of PTHrP corresponding to amino acids 1 to 34 of Table 2 |
| CGRP | Rat calcitonin gene-related peptide |
| TFA | Trifluoroacetic acid. |

EXAMPLE 1

Biological Assay for PTHrP Activity

The biological assay makes use of the dose-dependent generation of cyclic AMP in osteoblast-like cells such as the widely available UMR 106-01 cell line (20–40), in response to PTH. There are several ways in which the assay can be carried out, including direct measurement of adenylate cyclase activity in membranes of homogenates of osteoblast-like cells, and assay of cyclic AMP generated by intact cells. For simplicity, convenience and to allow ready assay of very large numbers of samples, we have assayed responses by growing UMR 106-01 cells as replicate cultures in 12-well plastic dishes, labelling the cellular ATP pool with $^3$H by pre-incubating for 2 hours with $^3$H-adenine, washing the cells briefly, then adding 1 mM isobutylmethylxanthine, a phosphodiesterase inhibitor. After 10 minutes reactions are stopped and $^3$H-cyclic AMP purified from incubates by sequential chromatography on DOWEX (a synthetic ion exchange resin made from styrene—divinylbenzene copolymers) and neutral alumina. The cells respond to PTH and to prostaglandins of the E series (principally $PGE_2$) with dose-dependent increases in cyclic AMP formation. This has been developed into a simple reproducible biological assay for PTH or PTH-like activity (34,40). The response to PTH, but not that to $PGE_2$, is inhibited in this system by prior incubation of samples with peptide antagonists of PTH (40) or other antiserum to PTH prepared against synthetic human PTH(1–34)(40).

EXAMPLE 2 pTHrP Activity Produced by BEN Cells

When BEN cell culture medium is assayed directly in the biological assay described in Example 1, it shows ability to stimulate cyclic AMP production. Activity is detectable in serial dilutions of medium, often in dilutions of as much as 1:100. Dilutions of crude culture medium stimulate activity parallel to that produced by PTH; pre-incubation of medium with goat anti-human PTH(1–34) results in no effect on PTHrP activity, although the same antiserum completely obliterates the activity of hPTH(1–34) itself (40). The synthetic peptides, [$^{34}$Tyr]hPTH(3–34)amide and [$^{34}$Tyr]hPTH(5–34)amide each inhibit the cyclic AMP response to PTHrP and to hPTH(1–34) in the UMR 106-01 cells, but these antagonists have no effect on the response to $PGE_2$ in the same cells (40).

Incubation of BEN cell medium with trypsin results in loss of biological activity of PTHrP, consistent with it being a protein. It is moderately heat-stable since it withstands a temperature of 100° C. for 2 minutes. Gel filtration of serum-free BEN cell conditioned medium on Biogel P60 in 0.1M acetic acid, with biological assay of effluent tubes, indicated that the activity resided in a macromolecule of molecular weight approximately 40,000. This proved later to be an over-estimate, probably as a result of association of the active material with other protein while in the crude state.

PTH radioimmunoassay was carried out with a number of different antisera—two with carbory-terminal specificity, one mid-molecule and one amino-terminal assay. In no case was immunoreactive PTH detected in BEN cell medium.

It was discovered that BEN cells could be grown to confluence, washed free of serum, and incubated for 24 hours in serum-free medium (50% DULBECCO's MODIFIED EAGLES' MEDIUM—50% Medium 199), with production of substantial amounts of PTHrP activity (detectable at dilutions of up to 1/100). This is therefore used as the standard method of accumulating large amounts of medium containing active material, which is stored at −20° C. until purification is begun.

EXAMPLE 3

Purification of PTHrP from BEN Cell Culture Medium

BEN cell medium (24-hour serum-free incubations) is accumulated and PTHrP activity determined by biological assay against human PTH(1–34) as standard, in the UMR 106-01 cyclic AMP response assay. Pooled batches of medium—5 liters at a time—are poured on to an SP SEPHADEX column (35 ml volume) after acidification to pH 4.8 with 1M acetic acid. After the column is extensively washed in 0.1M sodium acetate pH 4.8, with measurements of $E_{280}$ being carried out on individual tubes, batch elution of protein is carried out by adding 250 ml batches of NaCl at 0.1, 0.2 and 0.3M, and 500 mls of 0.5M. Biological activity is assayed in 100 µl samples of individual column tubes, and the bulk of biological activity is obtained by pooling the 0.5M NaCl fractions. The recovery of biological activity in this step is 90–100% and achieves a ten-fold purification. It serve's as a useful concentration method rather than as a substantial purification step.

The pooled active material from such a 5 liter step is referred to as SP1, SP2, etc. The active pool (0.5M NaCl) is acidified with TFA to a concentration of 0.1% and pumped onto a Reverse Phase HPLC (RP 300) column from which it is eluted using an acetonitrile gradient of 0.66% per minute. Individual column fractions from the RP300 column eluate (10 µl per 1 ml fraction) are bioassayed and the active fractions pooled and rotary evaporated. The recovery at this step is 60%. Six such SP pools are combined for the next step in purification, which therefore represents 30 liters of culture medium.

A protein estimate is carried out by the Bradford method (56) using BSA as standard, and the material is applied in batches of two milligrams to a HPLC VYDAC C18 column (10µ, 2.54×22 cm) from which it is eluted in an acetonitrile gradient of 0.5% per minute. Two peaks of biological activity are obtained consistently from the VYDAC column, peak A at 32% acetonitrile and peak B at 37% acetonitrile. Peak B is less contaminated with other protein than peak A, and is routinely chosen for further purification. The total recovery of activity is 30%. Peak A:Peak B ratios vary between batches from 2:1 to 0.5:1.

Peak B material is pooled and applied to a wide pore (300 Å) BAKERBOND C18 reversed phase column and eluted in an acetonitrile gradient (FIG. 1A). Absorbance is monitored at 215 nm. Individual column fractions are bioassayed, and the fractions containing the highest activity (fractions 50–55) are pooled. The active material is further purified by reversed phase HPLC using modified elution conditions (shallower acetonitrile gradient of 0.33% acetonitrile per minute), as shown in FIG. 1B. Hatched areas of FIG. 1 indicate biological assay data in µg equivalents of human PTH(1–34) and column fraction tube numbers 28 through 38 are indicated. Peak biological activity is found in fraction 31, corresponding to one of four closely situated protein peaks. The contents of fraction 31 were used for amino acid sequence determination and SDS-PAGE analysis. Initial sequence determination of this material identified amino acids 1 to 24 of Table 1.

The peak fraction was analysed by SDS-PAGE with a portion of the gel used to detect protein bands by silver-staining. The remainder of the gel was sliced into strips and the material eluted from gel slices assayed for biological activity.

Application of 20% of fraction 31 (approximately 6 pMoles, or 120 ng) to a 17% polyacrylamide gel resulted in a major band of silver-staining material, corresponding to a molecular weight of 18–19K as determined by molecular weight standards (FIG. 2). Two faint bands were seen at 35K and 67K, these possibly being dimers and tetramers of PTHrP. When a duplicate gel was sliced into 3 mm wide sections and eluted with 0.1% SDS, the only eluted activity was found in a single band corresponding to the silver-staining peak at 18–19K (FIG. 3). The amount applied to the gel was equivalent to 1.4 µg of hPTH(1–34) by biological assay. Protein estimation was not carried out directly, but calculated from amino acid sequencing data.

Specific biological activity of the pure material used for sequencing was estimated to be 6 µg equivalents of bovine PTH(1–34) per µg PTHrP protein (FIG. 3).

In a separate purification batch, the bioactive material recovered from HPLC step B (FIG. 1, fractions 31–32) was combined and re-chromatographed on a wide pore (300 A) BAKERBOND C$_{18}$ reversed phase column in an acetonitrile gradient at a rate of 0.33% per minute. As shown in FIG. 4, a single, sharply defined peak, peak 47, contains a protein of molecular weight 18K–19K. No other contaminant proteins, as determined by SDS-PAGE are detectable in this fraction. This material was biologically active, according to the assay set forth in Example 1, and was used for amino acid sequence determination using an Applied Biosystems Gas Phase Microsequencer. Sequence determination of this material identified 41 amino acids as set forth in the following Example.

EXAMPLE 4

Partial Sequence Determination of PTHrP

Purified PTHrP produced according to Example 3 was subjected to sequential Edman degradation and analysis using an Applied Biosystems gas phase sequenator (57). Sequence determination was performed in triplicate, giving the results set forth in Table 1. Forty-one amino acids are identified by N-terminal sequence analysis of purified PTHrP. The amino acid sequence of PTHrP was extended to residue 50 using tryptic fragments of PTHrP. The amino acids of Table 1 are designated using the one letter code (58).

Tryptic digestion of purified PTHrP was carried out by incubating 75 µg of PTH-like bioactivity (PTH-like bioactivity is determined by assaying preparations of PTHrP in the UMR-106 cell biological assay, against a synthetic PTH standard), with trypsin (1:10 w/w) for 24 hours at 37° C. This tryptic digest was resolved into 18 peaks on HPLC (FIG. 5). The amino acid. sequences of several of these peaks were determined and the sequence contained in peak 7 was found to overlap with the NH$_2$-terminal sequence of PTHrP, beginning at residue 38. This peptide extended the amino acid sequence of PTHrP to residue 50.

The first 24 amino acids of PTHrP were compared with protein sequences in the NBRF data base (59) using a computer programme. Substantial homology with the first 24 amino acids of human and rat PTH was revealled, with an overall sequence identity of 45–80%. Structural similarity is particularly marked with the first 13 amino acids of human PTH, and much less so thereafter. It is known that the sequence containing the first 10 amino acids of PTM is very weakly immunogenic, and indeed this can be predicted from the actual sequence and using a computerized prediction method. When the PTHrP sequence is analysed in the same way, it is found to be appreciably more immunogenic than PTH.

TABLE 1

| PTHrP AMINO ACID SEQUENCE |
|---|
| 1 10 20 |
| A V S E H Q L L H D K G K S I Q D L R R R F F L H |
| 30 40 50 |
| H L I A E I H T A E I R A T S E - S - N |
| A T S E V S P N G K P - P |
| TRYPTIC PEPTIDE |

EXAMPLE 5

Amino Acid Analysis of Purified PTHrp

A highly purified sample of PTHrP (tubes 46 and 48 from the column eluate of FIG. 4; total PTH-like bioactivity 7 µg) was chromatographed on a Brownlee C8 column (2.1 mm) as shown in FIG. 6. Diode array detection of the major peak (inset of FIG. 6) showed contamination in the peak shoulders with aromatic amino acid content. The central portion of the major peak was hydrolyzed for 25 hours at 110° C. and analysed in a Beckman 6300 Amino Acid Analyser. The results are shown in Table 2. The amount analysed was 20 pmoles, and was found to be equivalent in biological activity to 8.8 μg of bovine PTH(1–34). This indicated that the specific activity of this purified preparation was in the order of 20 times greater than that of PTH. The amino acid analysis indicates that PTHrP contains 154 amino acids.

TABLE 2

Amino-Acid Composition of Purified PTHrP

| Amino Acid | Residues (Sample) | Residues (Theoretical) |
|---|---|---|
| Asp | 12.60 | 12 |
| Thr | 10.40 | 12 |
| Ser | 11.40 | 14 |
| Glu | 22.14 | 17 |
| Gly | 13.02 | 10 |
| Ala | 7.99 | 5 |
| Val | 3.69 | 5 |
| Ile | 4.97 | 4 |
| Leu | 11.35 | 12 |
| Nle | 0.0 | 0 |
| Tyr | 1.88 | 2 |
| Phe | 3.11 | 3 |
| His | 7.10 | 8 |
| Lys | 21.11 | 17 |
| Arg | 10.76 | 12 |
| Pro | 12.01 | 7 |
| TOTAL | 153.57 | 140 |

EXAMPLE 6

Peptide Synthesis of pTHrP Peptides and the Production of Antisera Against these Peptides Synthetic peptides corresponding to the amino-terminal sequence of PTHrP were synthesized by the Merrifield procedure (41) using an Applied Biosystems Model 430A automatic peptide synthesizer. The synthetic peptides were cleaved from the resin using anhydrous HF (42), extracted with 60% acetonitrile and 0.1% trifluoroacetic acid, rotary evaporated, lyophilized and chromatographed on a low pressure reversed phase column (2.5×30 cm, Amicon $C_{18}$ reversed phase, 15–70 μ250 A pore size ) with a gradient of 0–60% acetonitrile (total volume 1000 ml). The purified peptide was lyophilized. Amino acid analysis was used to confirm the composition of peptides. Rabbits were immunized with synthetic peptide conjugated to soya bean trypsin inhibitor via a carboxyl-terminal cysteine (43).

Based on the sequence information in Table 1 the following peptide analogs were synthesized:

Ala-Val-Ser-Glu-His-Gln-Leu-Glu-His-Asn-Cys ([$Glu^8$, $Asn^{10}$,$Cys^{11}$] PTHrP (1–11), Ala-Val-Ser-Glu-His-Gln-Leu-Leu-His-Asn-Lys-Gly-Lys-Ser-Ile-Gln ([$Asn^{10}$] PTHrP(1–16)), [$Asn^{10}$,$Tyr^{17}$]PTHrP(1–17), and PTHrP(1–34). The analogs, [$Glu^8$, $Asn^{10}$, $Cys^{11}$] PTHrP(1–11) and [$Asn^{10}$] PTHrP(1–16) were inactive in the adenylate cyclase assay and did not antagonize the action of PTH itself or of conditioned medium from BEN cells. [$Glu^8$,$Asn^{10}$,$Cys^{11}$] PTHrP(1–11) conjugated to soya bean trypsin inhibitor was used to immunize rabbits, and an antiserum produced which was used in radioimmunoassay. An antiserum against [$Asn^{10}$]PTHrP(1–16) was also raised in a similar manner in rabbits.

EXAMPLE 7

Assays Using Antisera Directed Against PTHrP

Radioimmunoassay was carried out using $I^{125}$-labelled [$Asn^{10}$,$Tyr^{17}$] PTHrP(1–17) as a tracer for radioimmunoassay, and rabbit antiserum produced in accordance with Example 5, at a final dilution of 1/1000. Primary incubations were carried out overnight at 4° C. in 0.05M sodium phosphate buffer, pH 7.5 containing 0.1% bovine serum albumin. Separation of bound from free peptide was performed using a solid phase second antibody (Sac Cell—Wellcome, Australia). Iodination of synthetic peptide was carried out as previously described for calcitonin (44) to an approximate specific activity of 150 μCi/μg.

As shown in FIG. 7A, the assay recognized PTHrP (1–10) and (1–16) equally. The cross-reactivities of hPTH(1–10) and hPTH(1–34) were 0.5 and 0.3% respectively. Cross-reactivity of rat PTH(1–34) and bovine PTH(1–34) and human PTH(1–34) were 7%, 5% and 0.4% respectively (FIG. 7B).

PTHrP may be purified by immunoaffinity chromatography using antibodies capable of binding to epitopes of PTHrP. In this technique, antibodies capable of binding PTHrP are attached to a support matrix. PTMrP containing material is percolated through the support matrix, when it is located in a chromatography column, or alternatively are mixed with the matrix if a batch approach is used. Any PTHrP present in the material binds to the matrix, which can be washed to remove any contaminant material. Purified PTHrP can then be eluted from the matrix using conditions which disrupt antibody binding, such as high or low pH conditions. A similar technique can be used to purify antibodies capable of binding to PTHrP. In this regard, the steps carried out are the same as those outlined above, except that PTHrP is attached to a support matrix.

FIG. 8 shows the application of radioimmunoassay to the HPLC fractions of partially purified PTHrP (i.e. the eluant of SP-Sephadex chromatography).

The partially purified PTHrP (equivalent to 35 μg bPTH) was chromatographed on a $C_{18}$ reverse phase guard column (RP300, 7μ 0.3×4.0 cm). Elution was carried out in a gradient of 0–60% acetonitrile/0.1% TFA at a rate of 1 ml/min over 90 minutes. Biological assay is represented an open circle (o), radioimmunoassay as a closed circle (o). FIG. 8 shows the coincident elution of biological and immunological activity.

The PTHrP (1–34) peptide was assayed against bovine PTH(1–34) in the cyclic AMP response in UMR 106-01 cells and was found to be of equivalent potency (FIG. 9A). Similarly, it was equivalent to bovine PTH(1–34) in ability to increase plasminogen activator activity in UMR 106-01 cells (FIG. 9B). This is a PTH response system which we have reported and fully characterized (52).

Western Blot Analysis:

Protein from two samples of peak A of Example 3, highly purified PTHrP derived from peak B of Example 3 and pure bovine parathyroid hormone were was subjected to SDS-PAGE, transferred to nitrocellulose, blocked with low detergent "Blotto" for 1 hour, incubated with rabbit antiserum against [$ASN^{10}$] PTHrP(1–16) (see sample 5) at a dilution of 1:200, incubated for 1 hour with a $^{125}$-labelled Fab fragment of goat anti-rabbit serum and autoradiographed (FIG. 10). As expected, lane 4 which contained highly purified PTHrP, shows a band of 18 Kd corresponding to the molecular weight of PTHrP. In contrast, lanes 2 and 3, which contain protein from peak A of Example 3, show bands of approximately 22 Kd. This strongly suggests that PTHrP exists in at least 2 forms, both of which possess the same biological potency, but differ in molecular weight, and elution behaviour on reverse phase HPLC. Pure bovine parathyroid hormone (lane 1) showed no band under these conditions.

Antibodies directed against PTHrP may be used to detect the presence or absence of this protein in a biological sample.

The biological sample may be bound to a solid support, such as nitrocellulose or PVC, and reacted with anti-PTHrP antibodies. Antibody binding may then be determined by using a detectable label attached to the antibodies, or rather by using a second label led reagent specific for bound antibodies. Reagents such as protein A, or anti-Fab or anti-Fc antibodies may be used.

Alternatively, the anti-PTHrP antibodies may be bound to a solid support such as PVC plates, polystyrene beads etc. The material to be assayed is then added to the support, which is incubated for a time sufficient to allow antibody binding, followed by the washing away of unbound material. A second labelled PTHrP antibody may then be added to the support to detect antibody binding. If the second antibody is not labelled, additional labelled reagents may be added to the support to detect antibody binding. As will be readily appreciated, this approach assumes that PTHrP contains at least two epitopes, one of which binds to antibody bound to the solid support, and the other which binds to a second antibody.

Suitable detectable labels include $^{125}$I, $^{32}$P, $^{3}$H, $^{14}$C, biotin, avidin, protein A, colloidal gold or silver, urease, alkaline phosphatase, horse radish peroxidase or phycobiliprotein.

EXAMPLE 7

Genetic Analysis

Since the PTHrP protein possessed substantial homology to PTH it was deemed necessary to determine whether it was encoded by a unique non-allelic gene or was a mutated form of the PTH gene itself.

Experiments were carried out using a probe specific to the single-copy PTH gene and the 3' flanking region (45), labelled with $^{32}$P. Northern gel analysis was carried out as described earlier (46) using 5 mg of PolyA$^+$ mRNA per track prepared from either BEN cells or from human parathyroid adenoma tissue removed in surgery. Southern gel analysis was a modification of the standard procedure (47) using 10 mg of restriction digested genomic DNA per track prepared from either BEN cells or from human leukocytes (48). The human PTH probe was random primed with $^{32}$P-nucleotides to a specific activity at greater $10^8$dpm/mg (26). Hybridization and washing conditions were as described (46).

Northern gel analysis of polyA+ messenger RNA showed that BEN cells did not express the PTH gene at detectable levels compared with parathyroid adenores tissue (not illustrated). Southern gel analysis of restriction digested genomic DNA from either BEN cells or from human leukocytes showed identical PTH-containing restriction fragments, for example 4.2 and 3.8 kb, EcoR1 fragments. Therefore, BEN cells contain both the non-expressed PTH gene and, by inference from the expression of PTHrP having the indicated protein sequence, an homologous gene encoding a PTH-related protein.

EXAMPLE 8

Production of PTHrP by Various Tissues

PTHrP production appears not to be confined to tumour cells. Experiments involving extracts of fetal lamb, ewe tissues and placenta have been performed to clarify this point. By carrying out the assays after pre-incuoation with anti-PTH antiserum or with PTH antagonist we were able to determine whether biological activity was due solely to PTH or to PTHrP, or to a mixture of the two.

It has been found that the fetal lamb parathyroid contained biological activity of which only 50% could be explained by PTH, the remainder possibly being due to PTHrP. Some PTHrP (approximately 20%) was found in maternal parathyroid.

Most strikingly, however, the placenta was found to contain appreciable amounts of activity, which could be explained entirely as PTHrP, and which behaved on HPLC in a similar fashion to PTHrP from BEN cell medium. Furthermore, the amount of PTHrP detectable in placenta was not diminished in placenta from ewes in whom the parathyroids were removed from fetuses. This suggests that the placenta might be an important source of PTHrP.

We have purified PTHrP from urine of patients with humoral hypercalcemia associated with malignancy (data not shown). On the basis of these results, PTHrP present in serum, urine or other biological fluids may be detected using the antibody reagents of the present invention. The antibody reagents of the present invention therefore have potential as diagnostic reagents in the identification of malignancy.

Other aspects of the present invention, and modifications and variations thereto, will become apparent to those skilled in the art on reading this specification, and all such other aspects and modifications and variations are considered as included within the scope of the present invention.

REFERENCES

1. Martin, T. J. and Atkins, D. (1979) Essays in Med. Biochem. 4, 49–82.
2. Mundy, G. R. and Martin, T. J. (1982) Metabolism 31, 1274–1277.
3. Mundy, G. R. Ibbotson, K. J., D'Suoza, S. M., Simpson, E. L., Jacobs, J. W. and Martin, T. J. (1984) New Eng. J. Med. 310, 1718–1727.
4. Albright, F. (1941) New Eng. J. Med. 225, 789–796.
5. Berson, S. A. and Yalow, R. S. (1966) Science 154, 907–909.
6. Powell, D., Singer, F. R., Murray, T. M., Mankin, C. and Potts, J. T. Jr. (1973) New Eng. J. Med. 289, 176–181.
7. Stewart, A. F., Horst, R., R., Deftos, L. J., Cadman, E. C., Lang, R. and Broadus, A. E. (1980) New Eng. J. Med. 903, 1377–1383.
8. Simpson, E. L., Mundy, g. R., D'Souza, S. M., Ibbotson, K. J., Bockman, R. and Jacobs, J. W. (1983) New Eng. J. Med 309, 325–332.
9. Ibbotson, K. J., D'Souza, S. M., Ng, K. W., Osborne, C. K., Niall, M., Martin, T. J. and Mundy, G. R. (1983) Science 221, 1292–1294.
10. Ibbotson, K. J., Harrod, J., Gowen, M., D'Suoza, S., Smith, D. D., Winkler, M. E., Derynck, R. and Mundy, G. R. (1986) Proc. Natl. Acad. Sci. USA 83, 2228–2232.
11. Tashjian, A. J. Jr., Voelkel, E. F., Lazzaro, M., Singer, F. R., Roberts, A. B., Derynck, R., Winkler, M. E. and Levine, L. (1985) Proc. Natl. Acad. Sci, USA 82, 4535–4538.
12. Stewart, A. F., Insogna, K. L., Goltzman, D. and Broadus, A. E. (1983) Proc. Natl. Acad. Sci, USA 80; 1454–1458.
13. Rodan, S. B., Insogna, K. L., Vignery, A. M. C., Stewart, A. F., Boradus, A. E., D'Souza, S. M., Bertolini, D. R., Mundy, G. R. and Rodsn, G. A. (1983) J. Clin. Invest. 72; 1511–1515.

14. Strewlet, G. J., Williams, R. D. and Nissenson, R. A. (1983) J. Olin. Invest. 71: 769–774.

15. Merendino, J. J., Insogna, K. K., Milstone, L. M., Broadus, A. E. and Stewart, A. F. (1986) Science 231, 388–390.

16. Rosol, T. J., Capen, C. C., Weisbrode, S. E. and Horst, R. L. (1986) Lab. Invest. 54, 679–688.

17. Ellison, M., Woodhouse, D., Hillyard, C. J., Dowsett, M., Coombes, R. C. Gilby, E. D., Greenberg, P. B. and Neville, A. M. (1975) Br. J. Cancer 32, 373–379.

18. Kohler et al., (1976) Eur. J. Immunol. 6, 11–19.

19. Kennet et al (1978) Current Topics in Microbiology and Immunology 81, 77–91.

20. T. J. Marin, P. M. Ingleton, J. C. E. Underwood, R. A. Melick, V. P. Michelangeli and N. H. Hunt. Parathyroid hormine responsive adenylate cyclase in an induced transplantable osteogenic sarcoma in the rat. Nature 260, 436–438 (1976).

21. D. Arkins, N. H. Hunt, P. M. Ingleton and T. J. Martin. Rat osteogenic sarcoma cells: isolation and effects of hormones on the production of cyclic AMP and cyclic GMP. Endocrinology, 101, 555–561, (1977).

22. D. Arkins and T. J. Martin. Rat osteogenic sarcoma cells: Effects of some prostaglandins, their metabolites and analogues on cyclic AMP production. Prostaglandins, 13, 861–871 (1977).

23. A. Crawford, N. H. Hunt, J. K. Dawborn, V. P. Michelangeli and T. J. Martin. Membranes from a transplantable osteogenic sarcoma responsive to parathyroid hormone and prostaglandins: regulation and adenylate cyclase and the hormone metabolism. J. Endocr., 77, 213,224, (1978).

24. A. Crawford, D. Arkins and T. J. Martin. Rat Osteogenic sarcoma cells: Comparison of the effects of prostaglandins $E_1$, $E_2$, $I_2$ (prostacyclin), 6 keto $F_{I\alpha}$, and thromboxane $B_2$ on cyclic AMP production and adenylate cyclase activity. Biochem. Biophys. Res. Comm., 82, 1195–1201, (1978).

25. Martin, P. M., Ingleton. L. A., Coulton and R. A. Melick, Metabolic properties of hormonally responsive osteogenic sarcoma cells. Clin. Orthop. Rel. Res., 140. 247–254, (1979).

26. D. Atkins, P. C. Waller and T. J. Martin. Rat osteogenic sarcoma cells: Modulation of hormone stimulated cyclic AMP production by prostaglandin antagonists and biosynthesis inhibitors. Clin. Exp. Pharm. and Phys., 7, 31–44 (1980).

27. N. C. Partridge, D. Alcorn, V. P. Michelangeli, B. E. Kemp, G. B. Ryan and T. J. Martin. Functional properties of hormonal responsive cultured normal and malignant rat osteoblastic cells. Endocrinology, 108, 213–219 (1981).

28. N. C. Partridge, B. E. Kemp, M. C. Veroni and T. J. Martin. Activation of cyclic AMP-dependent protein kinase in normal and malignant bone cells by parathyroid hormone, prostaglandin $E_2$ and prostacyclin. Endocrinology, 108, 220–226 (1981).

29. N. C. Partridge, R. J. Frampton, J. A. Elsman, V. P. Michelangeli, E. Elms., T. R. Bradley and T. J. Martin. Receptors for $1,25(OH)_2$ vitamin $D_3$ enriched in cloned osteoblast-like rat osteogenic sarcoma cells. FEBS Letters, 115, 139–142 (1980).

30. N. C. Partridge, B. E. Kemp, S. A. Livesay and T. J. Martin. Activity ratio measurements reflect intracellular activation of cyclic AMP-dependent protein kinase in osteoblasts. Endocrinology, 111, 178–183 (1982).

31. S. A. Livesay, B. E. Kemp, C. A. Re, N. C. Partridge, and T. J. Martin. Selective hormonal activation of cyclic AMP-dependent protein kinase isoenzymes in normal and malignant osteoblasts. J. Biol. Chem., 257, 14983–14988 (1982).

32. N. C. Partridge, D. Alcorn, V. P. Michelangeli, G. Ryan and T. J. Martin. Morphological and biochemical characterization of four clonal osteogenic sarcoma cell lines of rat origin. Cancer Res. 43, 4308–4314, (1983).

33. J. A. Hamilton, S. R. Lingelbach, N. C. Partridge and T. J. Martin. Stimulation of plasminogen activator in osteoblast-like cells by bone-resorbing hormones. Biochem. Biophys. Res. Comm., 122, 230–236 (1984).

34. S. M. Forrest, K. W. Ng, D. M. Findlay, V. P. Michelangeli, S. A. Livesey, N. C. Partridge, J. D. Zajac and T. J. Martin. Characterization of an osteoblast-like clonal line which responds to both parathyroid hormone and calcitonin. Calc. Tiss. Int. 37, 51–56 (1985).

35. M. Kubota, K. W. Ng and T. J. Martin. Effect of 1,25-dihydroxyvitamin $D_3$ on cyclic AMP responses to hormones in clonal osteogenic sarcoma cells. Biochem. J., 231, 11–17 (1985).

36. N. C. Partridge, A. L. Opie, R. T. Opie and T. J. Martin. Inhibitory effects of parathyroid hormone on growth of osteogenic sarcoma cells. Calc. Tiss. Int., 37, 519–525 (1985).

37. K. W. Ng, S. A. Livesey, F. Collier, P. Gummet and T. J. Martin. Effect of retinoids on the growth, ultrastructure of cytoskeletal structures of malignant osteoblasts. Cancer Res. 45, 5106–5113 (1985).

38. S. A. Livesey, K. W. Ng. G. Collier, M. Kubota, A. L. Steiner and T. J. Martin. Effect of retonoic acid on cellular content and PTH activation of cyclic AMP-dependent protein kinase isoenzymes in clonal osteogenic sarcoma cells. Cancer Res. 45, 5734–5741 (1985).

39. J. A. Hamilton, S. R. Lingelbach, N. C. Partridge, and T. J. Martin. Hormone regulation of plasminogen activator production by bone-resorbing hormones in normal and malignant osteoblasts. Endocrinology, 116, 2186–2191 (1985).

40. M. Kubota, K. W. Ng, J. Murase, T. Noda, J. M. Moseley and T. J. Martin. Efficacy and specificity of human parathyroid hormone analogues as antagonists in intact clonal osteogenic sarcoma cells. J. Endocrinol. 108, 261–265 (1986).

41. Hodges, R. S. and Merrifield, R. B. (1975) Anal. Biochem. 65, 241–272.

42. Stewart, J. M. and Young, J. P. (1966) Solid Phase Peptide Synthesis pp. 44; 66, Freeman, San Francisco.

43. Carlsson, J., Drevin, H. and Axen, R. (1978) Biochem. J. 173, 723–737.

44. Finalia),, D. M., DeLuise, J. Michelangeli, V. P., Ellison, M. and Martin, T. J. (1980) Cancer Res. 40, 1311–1317.

45. Vasicek, T. J., McDevitt, B. E., Freeman, M. W., Fennick, B. J., Hendy, G. N., Potts, J. T. Jr., Rich, A. and Xronenberg, H. M. (1983) Proc. Natl. Acad. Sci. USA 80, 2127–2131.

46. Zajac, J. D., Martin, T. J., Hudson, P., Niall, H. D. and Jacobs, J. W. (1985) Endocrinology 116, 749–755.

47. Reed, K. C. and Mann, D. A. (1985) Nucleic Acids Res. 13, 7207–7221.

48. Weeks, D. R., Beerman, N. and Griffiths, O. M. (1986) Anal. Biochem. 152, 376–385.

49. Hudson, P., Haley), J., John, M. Cronk, M., Crawford, R., Haralambidis, J., Tregear, G. W., Shine, J. and Niakkm H. D. (1983) Nature 301, 628–631.

50. Yalow, R. and Betson, S. A. (1959) Nature (Lond.), 184, 1648–1650.

51. Towbin, H., Stackelin, T. and Gordon, J. (1979) Proc. Natl. Acad. Sci. USA, 76, 4350–4354.

52. Allan, E. H., Hamilton, J. A., Medcalf, R. L., Kubota, M. and Martin, T. J. (1986) Biochim, Biophys. Acta., 888, 199–207.

53. Schold, M., Colombero, D., Reyes, A. and Wallace, B. (1984) DNA, Vol. 3, 6, 469–477.

54. Rabbani, S. A. Mitchell, J., Roy, D. A., Kramer, R., Bennett, H. P. J. and Soltryman, D. (1986) Endocrinology 118, 1200–1209.

55. Stewart, A. F., Insogna, K. L., Geltzman D. and Broadus, A. E. (1983) Proc. Natl. Acad. Sci. USA, 80, 1454–1458.

56. Bradford, M. (1976) Anal. Biochem. 72, 248–254.

57. Wettenhall, R. E. H., Kudlicki, W., Kramer, G. and Hardeshy, B. (1986) J. Biol. Chem. 261, 12444–12447.

58. IUPAC—IUB Joint Commission on Biochemical Nomenclature, (1985) J. Biol. Chem. 260, 14–42.

59. National Biochemical Research Foundation, Georgetown University Medical Center, 3900, Reservoir Rd, N.W., Washington, D.C. 20007.

We claim:

1. A method for the detection of parathyroid hormone related protein or fragments thereof in a given protein containing sample, comprising contacting the sample, or a support matrix onto which protein in the sample is immobilized, with antibody reagents that bind to epitopes of parathyroid hormone related protein and that bind to epitopes of said fragments, and subsequently detecting the presence or absence of antibody binding;

wherein said parathyroid hormone related protein to be detected has the following characteristics:

(a) an N-terminal amino acid sequence A V S E H Q L L H D K G K S I Q D L R R R F F L H H L I A E I H T A E I R A T S E —S—N; and (b) a molecular weight between 15 to 25 kilodaltons, as determined by sodium dodecyl polyacrylamide gel electrophoresis under reducing and non-reducing conditions.

2. A method as claimed in claim 1 wherein the antibodies that bind epitopes of parathyroid hormone related protein are labelled with a detectable marker.

3. A method as claimed in claim 1, wherein the presence or absence of antibody binding to parathyroid hormone related protein, is detected by reagents labelled with a detectable marker that binds to antibodies.

4. A method for the detection of parathyroid hormone related protein or fragments thereof in a given sample, comprising incubating the sample with a support matrix, onto which antibodies that bind epitopes of parathyroid hormone related protein are bound, for a time sufficient to allow antibody binding, and thereafter detecting the presence or absence of bound parathyroid hormone related protein with antibody reagents that bind to epitopes of parathyroid hormone related protein and that bind to epitopes of said fragments;

wherein said parathyroid hormone related protein to be detected has the following characteristics:

(a) an N-terminal amino acid sequence A V S E H Q L L H D K G K S I Q D L R R R F F L H H L I A E I H T A E I R A T S E —S—N; and (b) a molecular weight between 15 to 25 kilodaltons, as determined by sodium dodecyl polyacrylamide gel electrophoresis under reducing and non-reducing conditions.

5. A method as claimed in claim 4, wherein the antibody reagents used to detect the presence or absence of parathyroid hormone related protein in a given sample are labelled with a detectable marker.

6. A method as claimed in claim 4, wherein the binding or absence of binding of antibody reagents to parathyroid hormone related protein is detected with reagents labelled with a detectable marker.

* * * * *